US009238216B2

(12) United States Patent
Kim et al.

(10) Patent No.: US 9,238,216 B2
(45) Date of Patent: Jan. 19, 2016

(54) CARBON-BASED PALLADIUM CATALYST OBTAINED BY USING IONIC LIQUID, METHOD FOR PREPARING THE SAME AND HYDROGENATION OF HYDROFLUOROCARBON USING THE SAME

(71) Applicant: KOREA INSTITUTE OF SCIENCE AND TECHNOLOGY, Seoul (KR)

(72) Inventors: Chang Soo Kim, Daegu (KR); Kyesang Yoo, Seoul (KR); Byoung Sung Ahn, Seoul (KR); Hyun Joo Lee, Gyeonggi-do (KR); Jeong Myeong Ha, Seoul (KR); Hong Gon Kim, Seoul (KR)

(73) Assignee: KOREA INSTITUTE OF SCIENCE AND TECHNOLOGY, Seoul (KR)

( * ) Notice: Subject to any disclaimer, the term of this patent is extended or adjusted under 35 U.S.C. 154(b) by 63 days.

(21) Appl. No.: 14/059,007

(22) Filed: Oct. 21, 2013

(65) Prior Publication Data

US 2015/0045589 A1   Feb. 12, 2015

(30) Foreign Application Priority Data

Aug. 7, 2013 (KR) .................. 10-2013-0093520

(51) Int. Cl.
| | |
|---|---|
| *B01J 23/44* | (2006.01) |
| *C07C 17/354* | (2006.01) |
| *C07C 19/08* | (2006.01) |
| *C07C 21/18* | (2006.01) |
| *B01J 37/03* | (2006.01) |
| *B01J 21/18* | (2006.01) |
| *B01J 35/00* | (2006.01) |
| *B82Y 30/00* | (2011.01) |
| *B01J 31/02* | (2006.01) |

(52) U.S. Cl.
CPC ............ *B01J 23/44* (2013.01); *B01J 21/18* (2013.01); *B01J 35/006* (2013.01); *B01J 35/0013* (2013.01); *B01J 35/0053* (2013.01); *B01J 37/035* (2013.01); *B82Y 30/00* (2013.01); *C07C 17/354* (2013.01); *B01J 31/0284* (2013.01)

(58) Field of Classification Search
CPC ........................................................ B01J 23/44
See application file for complete search history.

(56) References Cited

U.S. PATENT DOCUMENTS 7,667,058 B2 * 2/2010 Anderson et al. ............. 554/141
2011/0021849 A1    1/2011 Avril et al.

FOREIGN PATENT DOCUMENTS

CN             102423704 A  *  4/2012

OTHER PUBLICATIONS

CN102423704A, Apr. 2012, pp. 1-6; English translation.*

(Continued)

*Primary Examiner* — Jafar Parsa
*Assistant Examiner* — Medhanit Bahta
(74) *Attorney, Agent, or Firm* — Ladas & Parry LLP

(57) ABSTRACT

Provided is a palladium on carbon (Pd/C) catalyst obtained by using an ionic liquid, a method for preparing the same, and a method for hydrogenation of hydrofluorocarbon using the same. More particularly, palladium particles are supported on carbon particles by using an ionic liquid, and the resultant Pd/C catalyst is used for hydrogenation of hydrofluorocarbon. The catalyst includes palladium particles having a smaller particle size and a more uniform shape as compared to the existing Pd/C catalysts, and thus shows high catalytic activity.

8 Claims, 3 Drawing Sheets

(56) References Cited

OTHER PUBLICATIONS

Mikkola, J-P, T. et al. Appl. Catal. A General 2007, 328, pp. 68-76.*
Zhao, X. et al. Int. J. of Hydrogen Energy 37 (2012) pp. 51-58.*
Yin, L. et al. Chem. Rev. 2007, 107, 133-173.*
Tarasenko, E. A. et al. Russ. Chem. Bull, Int. Ed. 2011, 60, pp. 179-181.*
Virtanen, P. et al. Chem. Eng. Science. 2007, 62, pp. 3660-3671.*
Kohler, K. et al. Chem. Eur. J. 2002, 8, pp. 622-631.*
Tae, H. et al. Appl. Chem. Eng. Feb. 2013, 24, pp. 82-86; English translation pp. 1-19.*
Hyunman Tae, et al; "Preparation of Palladium on Carbon for Hydrogenation Catalyst Using [Bmim][CF$_3$SO$_3$] as an Effective Solvent", Appl. Chem. Eng., vol. 24, No, 1, pp. 82-86; Published Feb. 2013.
John Meurig Thomas, et al; "High-Performance Nanocatalysts for Single-Step Hydrogenations", Acc. Chem. Res., vol. 36 (1), pp. 20-30; Publication Date: (Web): Oct. 11, 2002.
Zuowei Xie; "Cyclopentadienyl-Carboranyl Hybrid Compounds: A New Class of Versatile Ligands for Organometallic Chemistry", Accounts of Chemical Research, vol. 36, No. 1, Published on Web Oct. 30, 2002; pp. 1-9.
Manfred T. Reetz, et al; "Phosphane-Free Palladium-Catalyzed Coupling Reactions: The Decisive Role of Pd Nanoparticles", Agnew. Chem. Int. Ed. vol. 29, No. 1, pp. 165-168; Article first published online Jan. 12, 2000.
Peter Wasserscheid, et al; "Ionic Liquids—New "Solutions" for Transition Metal Catalysis", Angew. Chem. Int. Ed., vol. 39 Issue 21, pp. 3772-3789; Article first published online: Oct. 27, 2000.
Thomas Welton; "Room-Temperature Ionic Liquids. Solvents for Synthesis and Catalysis", Chem. Rev. vol. 99, pp. 2071-2083; Published on Web Jul. 7, 1999.
Sang-Wook Kim, et al; "Fabrication of Hollow Palladium Spheres and Their Successful Applications to the Recyclable Heterogeneous Catalyst for Suzuki Coupling Reactions", J. Am. Chem. Soc. vol. 124, pp. 7642-7643; Published on Web Jun. 8, 2002.
M. Fernandez-Garcia, et al; "Influence of Ceria on Pd Activity for the CO+O$_2$ Reaction", Journal of Catalysis, vol. 187, pp. 474-485; Oct. 25, 1999.
Y. Nishihata, et al; "Self-regeneration of a Pd-perovskite catalyst for automotive emissions control", Nature; vol. 418, pp. 164-167, Jul. 11, 2002.
Yin Li, et al; "Suzuki Cross-Coupling Reactions Catalyzed by Palladium Nanoparticles in Aqueous Solution", Organic Letters, vol. 2, No. 15, pp. 2385-2388; Published on Web Jun. 29, 2000.

* cited by examiner

CARBON-BASED PALLADIUM CATALYST OBTAINED BY USING IONIC LIQUID, METHOD FOR PREPARING THE SAME AND HYDROGENATION OF HYDROFLUOROCARBON USING THE SAME

CROSS-REFERENCE TO RELATED APPLICATIONS

This application claims priority under 35 U.S.C. §119 to Korean Patent Application No. 10-2013-0093520 filed on Aug. 7, 2013 in the Korean Intellectual Property Office, the disclosure of which is incorporated herein by reference in its entirety.

TECHNICAL FIELD

The following disclosure relates to a palladium on carbon (Pd/C) catalyst and a method for preparing the same. The following disclosure also relates to a method for hydrogenation of hydrofluorocarbon using the Pd/C catalyst.

BACKGROUND

Active studies have been conducted continuously to develop novel refrigerants substituting for the existing refrigerants due to the destruction of the ozone layer and the problem of global warming.

Chlorofluorocarbon (CFC) compounds, which are not toxic to the human body and non-combustible, have high thermal and chemical stability, and thus are used widely in various industrial fields, including refrigerants, foaming agents, spraying agents, cleaning agents, or the like. CFC is also referred to as freon gas. CFC was discovered by Thomas Midgley (US) in 1928. However, since it was shown that CFC is broken into chlorine atoms by the solar UV rays to serve as a main cause of the destruction of the ozone layer, use of CFC has been restricted by the international regulation. Therefore, many studies which are conducted to develop novel refrigerants substituting for CFC have resulted in the finding of hydrofluorocarbon (HFC). HFC compounds include HFC-134a, HFC-152a, HFC-32, HJC-125, or the like. Among those, HFC-134a used widely as a refrigerant for cars has a low index of destruction of the ozone layer but is problematic in that it has a high global warming index, and thus EU prohibits the use of HFC-134a. It seems that the use of HFC-134a is gradually prohibited all over the world. Therefore, there has been a need for a novel refrigerant which does not adversely affect global warming as well as the destruction of the ozone layer. As an alternate refrigerant, 2,3,3,3-tetrafluoro-1-propene (HFO-1234yf), one of the HFC compounds, shows a low effect upon the destruction of the ozone layer and global warming, and thus is given many attentions as an eco-friendly refrigerant. HFO-1234yf is produced through a 4-step process including a hydrogenation of hexafluoropropylene (HFP) [K. Avril, B. Collier, U.S. Pat. No. 0,021,849 A1 (2011)]. Consequently, there is an imminent need for developing a high-quality catalyst for each step to accomplish cost-efficient production of HFO-1234yf.

Palladium is an active material used for various reaction steps and is used, for example, for a hydrogenation/dehydrogenation, removal of contaminants from car exhaust and cracking of petroleum [M. Fernandez-Garcia, A. Martinez-Arias, L. N. Salamanca, J. M. Coronado, J. A. Anderson, J. C. Conesa, and J. Soria, J. Catal., 187, 474 (1999); Y. Nishihata, J. Mizuki, T. Akao, H. Tanaka, M. Uenishi, M. Kimura, T. Okamoto, and N. Hamada, Nature, 418, 164 (2002); J. M. Thomas, B. F. G. Johnson, R. Raja, G. Sankar, and P. A. Midgley, Acc. Chem. Res., 36, 20 (2003)]. Particularly, palladium is used widely as a catalyst for organic synthesis reactions including a generation of a large amount of carbon-carbon bonds, such as Suzuki, Heck and Stille reaction [M. T. Reetz, and E. Westermann, Angew. Chem, Int. Ed., 39, 165 (2000); Y. Li, X. M. Hong, D. M. Collard, and M. A. EI-Sayed, Org. Lett., 2, 2385 (2000); S.-W. Kim, M. Kim, W. Y. Lee, and T. Hyeon, J. Am. Chem. Soc., 124, 7642 (2002)]. Herein, it is to be noted that the size and shape of a palladium catalyst become an important factor in determining the quality of catalyst for a reaction. For this, many studies have been conducted to provide palladium having various shapes. In most cases, many different organic solvents and surfactants are used. However, since such organic solvents are not eco-friendly, many attentions are given to an ionic liquid as a new eco-friendly solvent.

An ionic liquid is formed of ions only, and generally includes nitrogen-containing cations and relatively smaller anions. By virtue of such a structure, an ionic liquid has a low melting point, thermal stability, low volatility and high ion conductivity, and shows high solubility to metals, organic substances and organometallic compounds [P. Wasserscheid, and W. Keim, Angew. Chem. Int. Ed., 39, 3773 (2000); T. Welton, Chem. Rev., 99, 2071 (1999)].

SUMMARY

An embodiment of the present invention is directed to providing a carbon-based palladium (Pd/C) catalyst having a uniform size and distribution to show high reaction activity and selectivity.

Another embodiment of the present invention is directed to providing a method for preparing a carbon-based palladium catalyst having a uniform size and distribution by using an ionic liquid as an eco-friendly solvent.

Still another embodiment of the present invention is directed to providing a method for preparing HFO-1234yf through hydrogenation of hexafluoropropylene (HFP) by using the carbon-based palladium catalyst as mentioned above.

In one general aspect, there is provided a Pd/C catalyst having a uniform size and distribution to show high reaction activity and selectivity.

The Pd/C catalyst is obtained by using an imidazole-based ionic liquid so that the palladium particles have a stabilized shape and uniform size.

The palladium particles may have an average particle diameter of 1-100 nm.

The content of palladium particles may be 0.9-5 wt % of carbon.

The Pd/C catalyst may be obtained by using an ionic liquid.

The ionic liquid may be an imidazole-based ionic liquid.

The imidazole-based ionic liquid may be at least one selected from the group consisting of 1-ethyl-3-methylimidazolium tetrafluoroborate, 1-butyl-3-methylimidazolium tetrafluoroborate, 1-hexyl-3-methylimidazolium tetrafluoroborate, 1-octyl-3-methylimidazolium tetrafluoroborate, 1-butyl-3-methylimidazolium hexafluorophosphate, 1-hexyl-3-methylimidazolium hexafluorophosphate, 1-octyl-1-3-methylimidazolium hexafluorophosphate, 1-butyl-3-methylimidazolium trifluoromethanesulfonate and 1-hexyl-3-methylimidazolium trifluoromethanesulfonate.

In another general aspect, there is provided a method for preparing a carbon-based palladium (Pd/C) catalyst for use in hydrogenation of hydrofluorocarbon, wherein the palladium particles have a small and uniformly controlled particle size by adding an ionic liquid when the carbon particles are impregnated with the palladium particles.

The method for preparing a carbon-based palladium (Pd/C) catalyst for use in hydrogenation of HFC includes the steps of:
(a) adding a palladium precursor to distilled water to provide an aqueous solution;
(b) adding an ionic liquid to the aqueous solution of (a);
(c) adding carbon particles to the mixed solution of (b);
(d) adding an aqueous solution of reducing agent dropwise to the mixed solution of (c);
(e) heating the mixed solution of (d) at 80-120° C. for 1-3 hours to obtain powder of a Pd/C catalyst; and
(f) washing the Pd/C catalyst with an organic solvent, followed by drying at 50-100° C. and sintering at 200-600° C. for 1-3 hours.

The palladium precursor and the ionic liquid may be used in a molar ratio of 0.1-3 (Pd precursor/ionic liquid)

The ionic liquid may be an imidazole-based ionic liquid.

The imidazole-based ionic liquid may be at least one selected from the group consisting of 1-ethyl-3-methylimidazolium tetrafluoroborate, 1-butyl-3-methylimidazolium tetrafluoroborate, 1-hexyl-3-methylimidazolium tetrafluoroborate, 1-octyl-3-methylimidazolium tetrafluoroborate, 1-butyl-3-methylimidazolium hexafluorophosphate, 1-hexyl-3-methylimidazolium hexafluorophosphate, 1-octyl-1-3-methylimidazolium hexafluorophosphate, 1-butyl-3-methylimidazolium trifluoromethanesulfonate and 1-hexyl-3-methylimidazolium trifluoromethanesulfonate.

In still another general aspect, there is provided use of the Pd/C catalyst for hydrogenation of hydrofluorocarbon (HFC).

The hydrogenation may be carried out at a temperature of 80-200° C. under a pressure of 0.1-2 atm.

The hydrofluorocarbon may be hexafluoropropylene (HFP) and 1,2,3,3,3-pentafluoropropene (HFO-1225ye).

The hydrogenation may provide 1,1,2,3,3,3-hexafluoropropane (236ea), and 1,2,3,3,3-pentafluoropropane (245cb) from HFP and 1,2,3,3,3-pentafluoropropene (HFO-1225ye).

The catalyst according to the present invention may be useful for hydrogenation of HFC, particularly for decomposition of hexafluoropropylene (HFP), and may be applicable to various hydrocarbon reactions in practice.

BRIEF DESCRIPTION OF THE DRAWINGS

The above and other aspects, features and advantages of the disclosed exemplary embodiments will be more apparent from the following detailed description taken in conjunction with the following figures.

DETAILED DESCRIPTION OF EMBODIMENTS

In one aspect, there is provided a carbon-based palladium (Pd/C) catalyst that catalyzes hydrogenation of hydrofluorocarbon (HFC). Herein, an example of HFC is HFC-134a, which is a refrigerant widely used for cars. However, use of HFC-134a has been restricted strictly because HFC-134a is a main cause of acceleration of global warming. Under these circumstances, HFO-1234yf has been suggested as a new eco-friendly refrigerant. As shown in the following Scheme 1, HFO-1234yf is produced through the steps of hydrogenation (HYD) and dehydrofluorination (De-HF) of hexafluoropropylene (HFP).

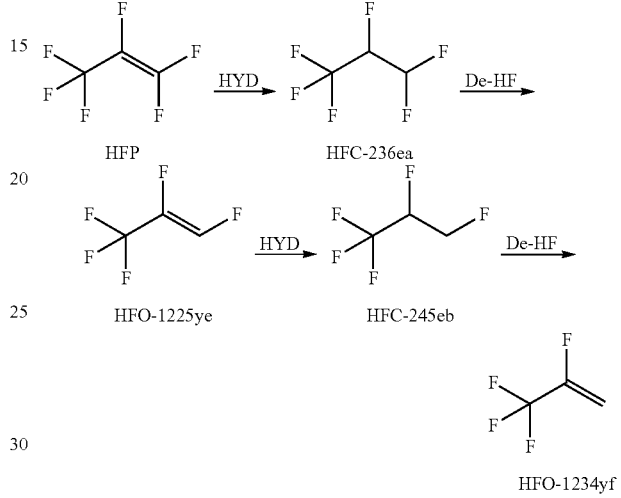

[Scheme 1]

The present invention is based on the finding that a Pd/C catalytic activity can be improved by producing palladium particles having a small and uniform particle shape and size through the use of an ionic liquid.

According to an embodiment, there is provided a Pd/C catalyst having a uniform size and distribution to show high reaction activity and selectivity.

The Pd/C catalyst includes palladium particles having a stabilized shape and a uniform size by virtue of the use of an imidazole-based ionic liquid.

The carbon may be at least one selected from the group consisting of Vulcan XC-72, acetylene black, Ketjen black, carbon nanopowder, carbon nanotubes, mesoporous carbon, carbon nanofibers and charcoal.

The palladium nanoparticles may have an average particle diameter of 1-100 nm.

The hydrofluorocarbon (HFC) may be hexafluoropropylene (HFP) and 1,2,3,3,3-pentafluoropropene (HFO-1225ye).

The content of palladium nanoparticles may be 0.9-5 wt % of carbon.

The ionic liquid may be an imidazole-based ionic liquid.

The imidazole-based ionic liquid may be at least one selected from the group consisting of 1-ethyl-3-methylimidazolium tetrafluoroborate, 1-butyl-3-methylimidazolium tetrafluoroborate, 1-hexyl-3-methylimidazolium tetrafluoroborate, 1-octyl-3-methylimidazolium tetrafluoroborate, 1-butyl-3-methylimidazolium hexafluorophosphate, 1-hexyl-3-methylimidazolium hexafluorophosphate, 1-octyl-1-3-methylimidazolium hexafluorophosphate, 1-butyl-3-methylimidazolium trifluoromethanesulfonate and 1-hexyl-3-methylimidazolium trifluoromethanesulfonate.

Figure 1:
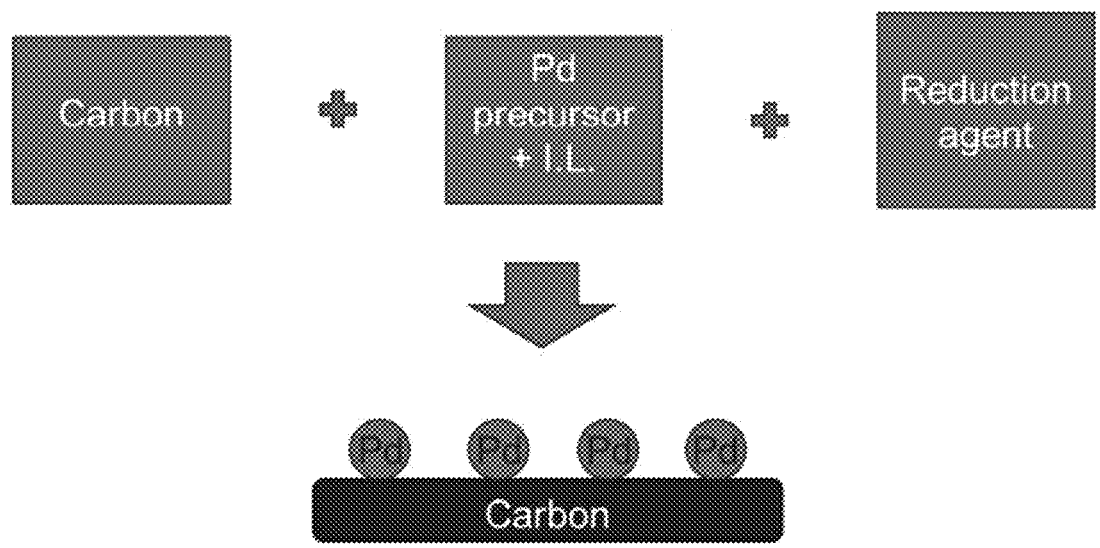
FIG. 1 is a schematic view showing the method for preparing a carbon-based palladium (Pd/C) catalyst according to an embodiment.
Figure 2:
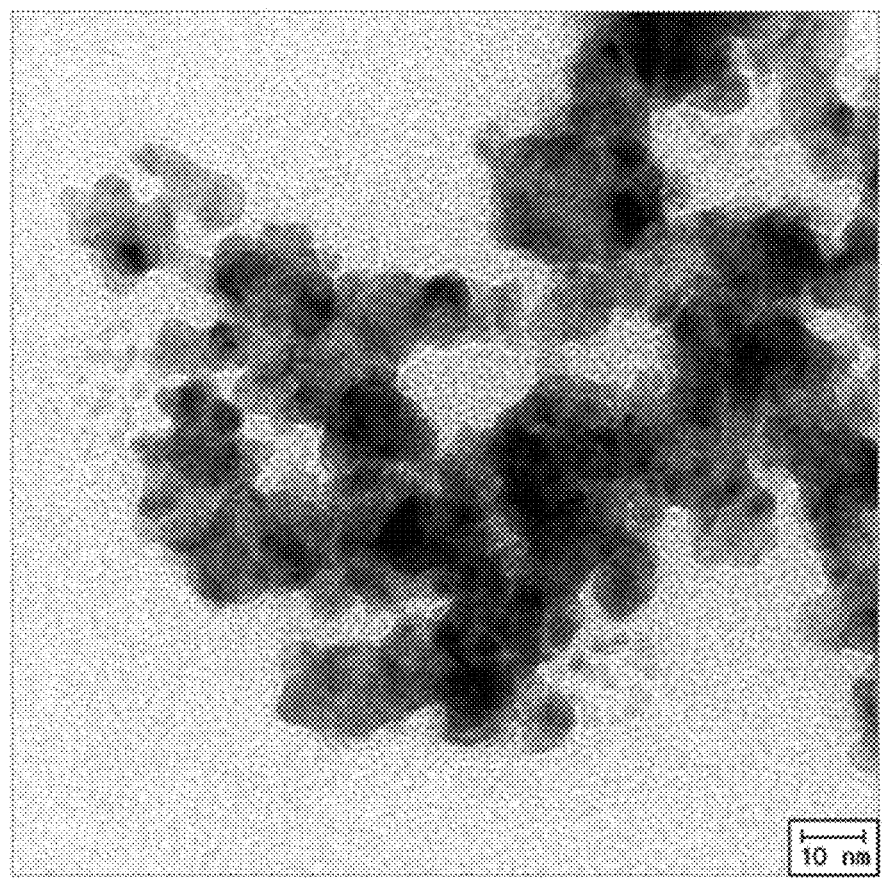
FIG. 2 is a transmission electron microscopy (TEM) image of a Pd/C catalyst obtained without an ionic liquid.
Figure 3:
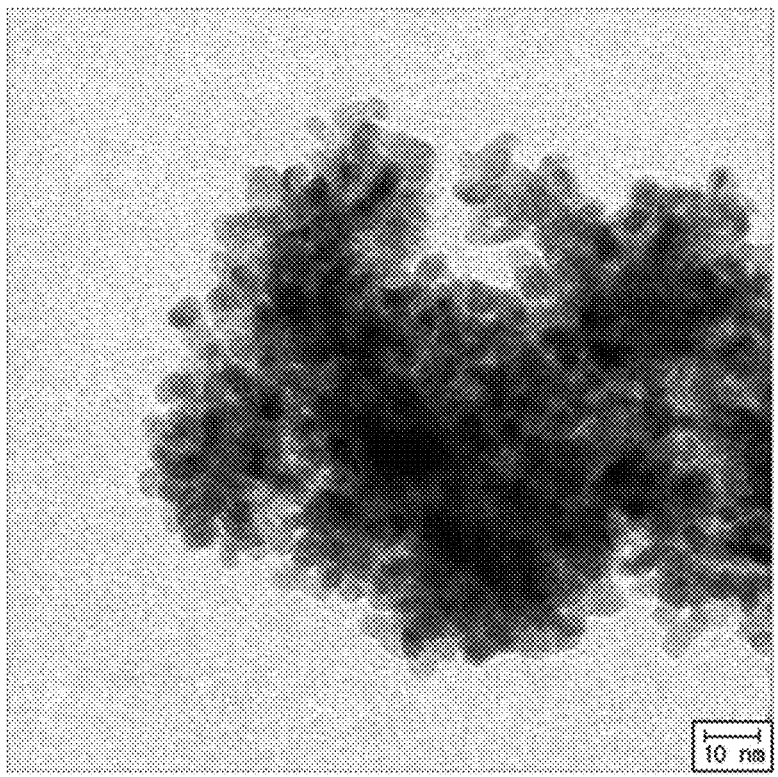
FIG. 3 is a TEM image of the Pd/C catalyst obtained by using 1-hexyl-3-methylimidazolium hexafluorophosphate (HPF6) as an ionic liquid according to an embodiment.
Figure 4:
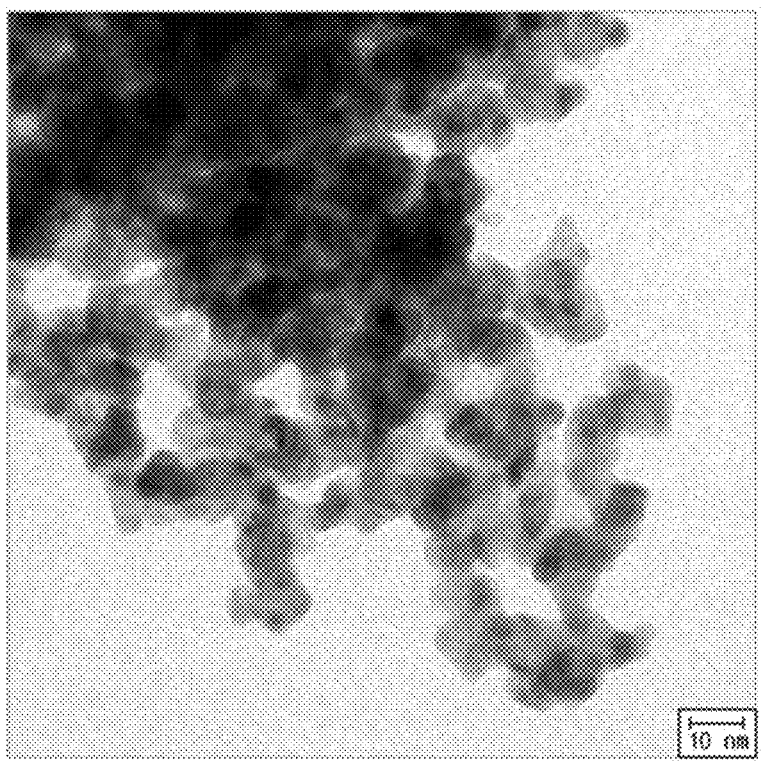
FIG. 4 is a TEM image of the Pd/C catalyst obtained by using 1-hexyl-3-methylimidazolium tetrafluoroborate (HBF4) as an ionic liquid according to an embodiment.
Figure 5:
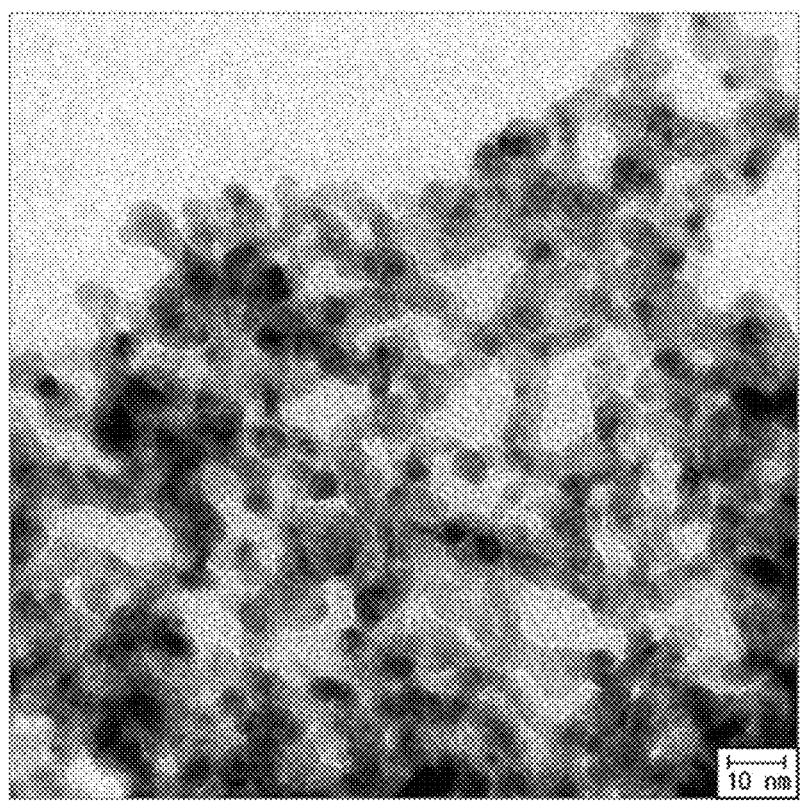
FIG. 5 is a TEM image of the Pd/C catalyst obtained by using 1-hexyl-3-methylimidazolium trifluoromethanesulfonate (HCF3) as an ionic liquid according to an embodiment.

As shown in FIG. 3-FIG. 5, the palladium nanoparticles supported on carbon according to an embodiment have a more stabilized shape and a smaller and more uniform size as compared to the catalyst obtained by using without an ionic liquid as shown in FIG. 1.

In another aspect, there is provided a method for preparing a Pd/C catalyst for use in hydrogenation of hexafluoropropylene, wherein the palladium particles have a small and uniformly controlled particle size by adding an ionic liquid when the carbon particles are impregnated with the palladium particles.

In order to prepare the carbon-based palladium catalyst having a small and uniform palladium particle size as disclosed herein, different steps are carried out under optimized conditions. As shown in FIG. 1, preparation of a Pd/C catalyst includes mixing a Pd precursor with distilled water to provide an aqueous solution. In another beaker, a reducing agent is mixed with distilled water to provide an aqueous solution. The aqueous solution of Pd precursor is mixed with an ionic liquid at a predetermined ratio while stirring at a constant speed. Then, carbon particles are added to the mixed solution under stirring. While stirring at a constant speed, an aqueous solution of reducing agent having the same molar ratio as the Pd precursor is added dropwise 1 ml to the mixed solution. Then, the precipitated catalyst powder is recovered by evaporation at 100° C. within 1 hour. Then, the catalyst powder is obtained by washing with a methanol, drying at 100° C. in an oven, and sintering at a predetermined temperature for 2 hours.

The reducing agent may be any one selected from the group consisting of hydrazine monohydride ($N_2H_4 \cdot H_2O$), sodium borohydride ($NaBH_4$) and formaldehyde (HCOH), and L(+)-ascorbic acid ($C_6H_8O_6$).

The carbon may be at least one selected from the group consisting of Vulcan XC-72, acetylene black, Ketjen black, carbon nanopowder, carbon nanotubes, mesoporous carbon, carbon nanofibers and charcoal.

In still another aspect, there is provided a use of Pd/C nanoparticles as a catalyst for hydrogenation of hydrofluorocarbon.

The hydrogenation may be carried out at a temperature of 80-200° C. under a pressure of 0.1-2 atm.

The hydrofluorocarbon may be hexafluoropropylene (HFP) and 1,2,3,3,3-pentafluoropropene (HFO-1225ye).

The hydrogenation may provide 1,1,2,3,3,3-hexafluoropropane (236ea), and 1,2,3,3,3-pentafluoropropane (245cb) from HFP and 1,2,3,3,3-pentafluoropropene (HFO-1225ye).

The catalyst according to the present invention has activity for HFP hydrogenation, and shows high activity and stability at a temperature of 50-200° C., particularly 100-140° C., under a pressure of 0.5-4 atm, particularly 1-2 atm. In addition, the catalyst may be used with a space velocity of reactants supplied to the reaction of 100-500,000 mL/g cath, particularly 2,500-50,000 mL/g cath.

Under a high space velocity condition, the conventional metal catalysts have reduced active spots and hardly maintain their catalytic activities. However, the catalyst according to the present invention has a broad and uniform area of active spots and shows high physical strength. It is thought that this is attributed to the control of the ionic liquid on agglomeration of palladium during synthesis of the catalyst so that palladium particles are distributed well on the surface of a carbon support to ensure a high catalytic activity.

EXAMPLES

The examples and experiments will now be described. The following examples and experiments are for illustrative purposes only and not intended to limit the scope of this disclosure.

Example 1

Preparation of Catalysts

A carbon-based palladium catalysts are obtained as follows. In a 50 mL beaker, 0.15 g of palladium tetrachloride ($Na_2PdCl_4$, 99.8%, Sigma Aldrich) is mixed with 10.5 mL of distilled water to provide an aqueous solution. In another 50 mL beaker, 0.020 g of sodium borohydride ($NaBH_4$, 99%, Sigma Aldrich) is mixed with 4.5 mL of distilled water to obtain an aqueous solution. The two types of aqueous solutions are mixed with each other to obtain a mixed solution. Then, 1.5 g of carbon powder (Sigma Aldrich) is added to the mixed solution while stirring. While stirring at a constant speed, a solution in which a reducing agent ($NaBH_4$) is dissolved in a molar ratio of $NaBH_4:Na_2PdCl_4$ of 1:1 is added dropwise to the mixed solution in an amount of 1 ml at a time. The precipitated catalyst powder is washed with distilled water, dried in an oven at 100° C., and sintered at 500° C. for 2 hours to obtain powder. The metal dispersibility and specific surface area of the obtained catalyst are measured by the hydrogen chemisorption method and the results are shown in the following Table 1.

TABLE 1

| Catalyst | Ionic liquid | Metal dispersibility (%) | Metal specific surface area ($m^2/g$) |
|---|---|---|---|
| BPF6-1 | [Bmim][PF6] | 1.57 | 7.45 |
| HPF6-1 | [Hmim][PF6] | 2.19 | 8.15 |
| OPF6-1 | [Omim][PF6] | 2.04 | 8.05 |
| EBF4-1 | [Emim][BF4] | 1.04 | 6.91 |
| BBF4-1 | [Bmim][BF4] | 1.24 | 7.04 |
| HBF4-1 | [Hmim][BF4] | 1.58 | 7.68 |
| OBF4-1 | [Omim][BF4] | 1.43 | 7.48 |
| BCF3-1 | [Bmim][CF3SO3] | 1.48 | 7.42 |
| HCF3-1 | [Hmim][CF3SO3] | 1.89 | 7.98 |

As shown in Table 1, when an ionic liquid contains a hexyl group at cationic part, the metal dispersibility and surface area become higher. At anionic part, better results are obtained in the order of PF6>CF3SO3>BF4. As for an ionic liquid, 'Bmim' means 1-butyl-3-methylimidazolium, 'Hmim' means 1-hexyl-3-methylimidazolium, 'Emim' means 1-ethyl-3-methylimidazolium, and 'Omin' means 1-octyl-3-methylimidazolium.

Example 2

Evaluation of Catalytic Performance for Hydrogenation

A test of catalytic performance for hydrogenation is carried out at a fixed-bed reactor made of stainless steel. First, 0.10 g of a catalyst is taken to be introduced to the reactor, and then pretreated at 200° C. for 2 hours while allowing $H_2$ gas to flow through the reactor at a flow rate of 20 ml. After the pretreatment, the internal temperature thereof is cooled to a room temperature. When the internal temperature of the reactor reaches a room temperature, hexafluoropropylene (HFP) and $H_2$ are allowed to flow through the reactor while maintaining a predetermined ratio of volumetric flow rates. After the reaction, the reaction mixture is analyzed by using gas chromatography (Agilent 6890) with a flame ionization detector (FID).

The catalysts obtained from Example 1 are used to carry out hydrogenation under the conditions of a pressure of 1 atm, a ratio of hydrogen/HFP of 0.6 and a GHSV of 48,000 mL/g cath. The results obtained by using different types of ionic liquids are shown in the following Table 2.

TABLE 2

HFP Conversion Depending on Type of Ionic Liquid

| Catalyst | HFP Conversion (%) |
| --- | --- |
| BPF6-1 | 40 |
| HPF6-1 | 60 |
| OPF6-1 | 55 |
| EBF4-1 | 20 |
| BBF4-1 | 25 |
| HBF4-1 | 30 |
| OBF4-1 | 25 |
| BCF3-1 | 45 |
| HCF3-1 | 50 |

As can be seen from Table 2, HPF6-1 catalyst provides the best result.

Example 3

Among the catalysts obtained from Example 1, HPF6-1 is prepared with a variable sintering temperature, and is used to carry out hydrogenation under the same conditions as described in Example 2. The results obtained by using different sintering temperatures are shown in the following Table 3.

TABLE 3

HFP Conversion Depending on Sintering Temperature of HPF6-1 Catalyst

| Sintering temperature (° C.) | HFP Conversion (%) |
| --- | --- |
| 100 | 25 |
| 150 | 30 |
| 200 | 40 |
| 300 | 50 |
| 400 | 55 |
| 500 | 60 |
| 550 | 40 |
| 600 | 5 |

As can be seen from Table 3, the highest conversion is obtained when HPF6-1 catalyst is sintered at 500° C.

Example 4

Among the catalysts obtained from Example 1, HPF6-1 is prepared with a variable palladium content, and is used to carry out hydrogenation under the same conditions as described in Example 2. It is to be noted that a ratio of flow rates of $H_2$/HFP is set to 1.25. The results obtained by using different palladium contents are shown in the following Table 4.

TABLE 4

HFP Conversion Depending on Palladium Content

| Catalyst | Palladium content (wt %) | HFP Conversion (%) |
| --- | --- | --- |
| HPF6-2 | 1.0 | 10 |
| HPF6-3 | 1.25 | 40 |
| HPF6-4 | 1.8 | 80 |
| HPF6-5 | 2.6 | 96 |
| HPF6-1 | 3.2 | 100 |
| HPF6-6 | 5.0 | 100 |

Example 5

Among the catalysts obtained from Example 1, HPF6-5 is prepared with a variable concentration of ionic liquid, and is used to carry out hydrogenation under the same conditions as described in Example 4. The results obtained by using different concentrations of ionic liquids are shown in the following Table 5.

TABLE 5

HFP Conversion Depending on Concentration of Ionic Liquid

| Catalyst | Pd Precursor/Ionic Liquid (mol/mol) | HFP Conversion (%) |
| --- | --- | --- |
| HPF6-7 | 0.1 | 95 |
| HPF6-8 | 0.25 | 93 |
| HPF6-9 | 0.5 | 90 |
| HPF6-10 | 0.75 | 93 |
| HPF-6-4 | 1.0 | 96 |
| HPF6-11 | 1.5 | 92 |
| HPF6-12 | 2.0 | 88 |
| HPF6-13 | 3.0 | 85 |

Example 6

Among the catalysts obtained from Example 1, HPF6-1 is used to carry out hydrogenation under the same conditions as described in Example 4. It is to be noted that hydrogenation is carried out with a variable ratio of flow rates of $H_2$/HFP. The results obtained by using different contents of reactants are shown in the following Table 6.

TABLE 6

HFP Conversion Depending on Ratio of Flow Rates of $H_2$/HFP

| Ratio of Flow Rates of $H_2$/HFP (ml/ml) | HFP Conversion (%) |
| --- | --- |
| 0.25 | 5 |
| 0.5 | 48 |
| 0.6 | 64 |
| 0.75 | 81 |
| 1.0 | 94 |
| 1.25 | 100 |
| 1.5 | 100 |

What is claimed is:

1. A method for preparing a carbon-based palladium (Pd/C) catalyst for hydrogenation of hydrofluorocarbon, the method comprising the steps of:
    (a) adding a palladium precursor to distilled water to provide an aqueous solution;
    (b) adding an ionic liquid to the aqueous solution of (a), wherein the ionic liquid is 1 hexyl-3-methylimidazolium hexafluorophosphate;

(c) adding carbon particles to the mixed solution of (b);
(d) adding an aqueous solution of a reducing agent dropwise to the mixed solution of (c);
(e) heating the mixed solution of (d) at 80-120° C. for 1-3 hours to obtain powder of the Pd/C catalyst; and
(f) washing the Pd/C catalyst with an organic solvent, followed by drying at 50-100° C. and sintering at 200-600° C. for 1-3 hours.

2. The method for preparing the carbon-based palladium (Pd/C) catalyst for hydrogenation of hydrofluorocarbon according to claim 1, wherein the Pd/C catalyst has a small and uniformly controlled particle size by adding an ionic liquid when the carbon particles are impregnated with palladium particles.

3. The method for preparing the carbon-based palladium (Pd/C) catalyst for hydrogenation of hydrofluorocarbon according to claim 2, wherein the palladium particles have an average particle diameter of 1-100 nm.

4. The method for preparing the carbon-based palladium (Pd/C) catalyst for hydrogenation of hydrofluorocarbon according to claim 1, wherein the palladium precursor and the ionic liquid are respectively used in a molar ratio of 0.1-3.

5. The method for preparing the carbon-based palladium (Pd/C) catalyst for hydrogenation of hydrofluorocarbon according to claim 1, wherein the ionic liquid further comprises at least one selected from the group consisting of 1-ethyl-3-methylimidazolium tetrafluoroborate, 1-butyl-3-methylimidazolium tetrafluoroborate, 1-hexyl-3-methylimidazolium tetrafluoroborate, 1-octyl-3-methylimidazolium tetrafluoroborate, 1-butyl-3-methylimidazolium hexafluorophosphate, 1-octyl-1-3-methylimidazolium hexafluorophosphate, 1-butyl-3-methylimidazolium trifluoromethanesulfonate and 1-hexyl-3-methylimidazolium trifluoromethanesulfonate.

6. The method for preparing the carbon-based palladium (Pd/C) catalyst for hydrogenation of hydrofluorocarbon according to claim 1, wherein the content of palladium is 0.9-5 wt % of the carbon particles.

7. The method for preparing the carbon-based palladium (Pd/C) catalyst for hydrogenation of hydrofluorocarbon according to claim 1, wherein the hydrogenation is carried out at a temperature of 80-200° C. under a pressure of 0.1-2 atm.

8. The method for preparing the carbon-based palladium (Pd/C) catalyst for hydrogenation of hydrofluorocarbon according to claim 1, wherein the hydrofluorocarbon is hexafluoropropylene (HFP) and 1,2,3,3,3-pentafluoropropene.

* * * * *